United States Patent [19]

Stache et al.

[11] 4,377,575

[45] Mar. 22, 1983

[54] CORTICOID-17-(ALKYL CARBONATES) AND PROCESS FOR THEIR MANUFACTURE

[75] Inventors: Ulrich Stache, Hofheim am Taunus; Werner Fritsch, Bad Soden am Taunus; Hans G. Alpermann; Jürgen K. Sandow, both of Königstein, all of Fed. Rep. of Germany

[73] Assignee: Hoechst Aktiengesellschaft, Frankfurt am Main, Fed. Rep. of Germany

[21] Appl. No.: 216,258

[22] Filed: Dec. 15, 1980

Related U.S. Application Data

[63] Continuation of Ser. No. 31,845, Apr. 20, 1979, abandoned.

[30] Foreign Application Priority Data

Apr. 25, 1978 [DE] Fed. Rep. of Germany ....... 2817988

[51] Int. Cl.³ .......................... A61K 31/56; C07J 5/00
[52] U.S. Cl. ................................. 424/243; 260/397.45
[58] Field of Search .................. 260/397.45; 424/241, 424/243

[56] References Cited

U.S. PATENT DOCUMENTS

| | | | |
|---|---|---|---|
| 3,558,675 | 1/1971 | Sarett et al. | 260/397.4 |
| 3,764,616 | 10/1973 | Elks et al. | 260/397.45 |
| 3,891,631 | 6/1975 | Phillipps et al. | 260/397.45 |
| 4,021,459 | 5/1977 | Green | 260/397.45 |
| 4,113,680 | 9/1978 | Kamano et al. | 260/397.45 |
| 4,242,334 | 12/1980 | Stache et al. | 424/243 |

FOREIGN PATENT DOCUMENTS

| | | |
|---|---|---|
| 742 | 2/1979 | European Pat. Off. |
| 1902340 | 9/1969 | Fed. Rep. of Germany |
| 1668451 | 8/1971 | Fed. Rep. of Germany |
| 2432408 | 1/1975 | Fed. Rep. of Germany |
| 2436747 | 2/1975 | Fed. Rep. of Germany |
| 2613875 | 10/1976 | Fed. Rep. of Germany |
| 885092 | 12/1961 | United Kingdom ........... 260/397.45 |
| 1253831 | 11/1971 | United Kingdom ........... 260/397.45 |
| 1480641 | 7/1977 | United Kingdom ........... 260/397.45 |

*Primary Examiner*—Elbert L. Roberts
*Attorney, Agent, or Firm*—Curtis, Morris & Safford

[57] ABSTRACT

What is disclosed are steroid-21-halogeno-17-(alkyl carbonates), useful as medicaments for the treatment of inflammatory dermatosis, and a method for making them.

13 Claims, No Drawings

CORTICOID-17-(ALKYL CARBONATES) AND PROCESS FOR THEIR MANUFACTURE

This is a continuation, of application Ser. No. 31,845, filed Apr. 20, 1979 now abandoned.

It is an object of the present invention to provide novel steroid-21-halogeno-17-(alkyl carbonates) of the formula I

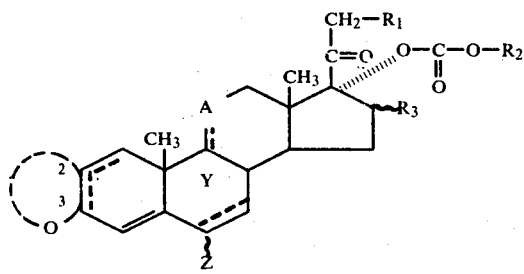

in which A denotes the groupings

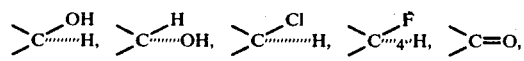

Y denotes hydrogen, fluorine or a chlorine atom,
Z denotes hydrogen, chlorine, fluorine or a methyl group,
$R_1$ denotes fluorine, chlorine, bromine or iodine,
$R_2$ denotes a linear or branched alkyl radical having from 1 to 10 carbon atoms,
$R_3$ denotes hydrogen, methyl in $\alpha$- or $\beta$-position, fluorine or a methylene group optionally substituted by one or two fluorine atoms,
optionally with additional double bonds in 1,2- and/or 2,3- and/or 6,7- and/or 9,11-position and

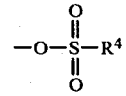

denotes a pyrazol ring, fused to positions 2 and 3 of the 3-desoxo-steroid skeleton, and optionally carrying a $C_1$-$C_4$ alkyl group or a possibly halogen-substituted phenyl group on one of the two nitrogen atoms.

It is a further object of the present invention to provide a process for the manufacture of a compound of the formula I, which comprises
(a) reacting a steroid-21-alkyl- or -aryl-sulfonate-17-(alkyl carbonate) of the formula I in which $R_2$, $R_3$, A, Y, Z, and

are as defined under formula I and $R_1$ denotes a radical of the formula $$-O-\overset{O}{\underset{\underset{O}{\|}}{\overset{\|}{S}}}-R^4$$

in which $R^4$ is $C_1$-$C_4$ alkyl, phenyl, methylphenyl, ethylphenyl, fluorophenyl, bromophenyl, chlorophenyl or nitrophenyl, with possible additional double bonds in 1,2- and/or 2,3- and/or 6,7- and/or 9,11-position, with a compound donating halogen anions, in the presence of inert organic solvents, and/or optionally aqueous media according to the phase transfer process, or (b) reacting a corticosteroid-17,21-(dialkyl orthocarbonate) of the formula II

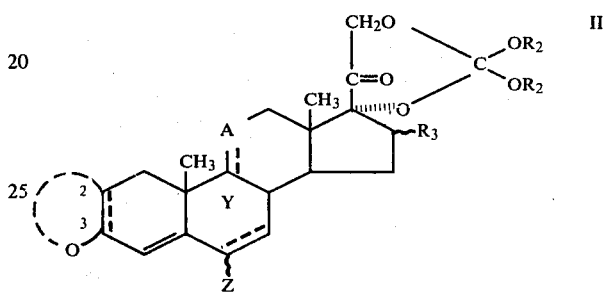

in which A, Y, Z,

$R_2$ and $R_3$ are as defined under formula I, with possible additional double bonds in 1,2- and/or 2,3- and/or 6,7- and/or 9,11-position, with halogen-donating inorganic or organic acid halides or with triphenylmethyl chloride in inert organic solvents.

The steroid-21-alkyl- or -aryl-sulfonate-17-(alkyl carbonates) of the formula I in which $R_1$ denotes an alkyl-, aralkyl- or optionally substituted aryl-sulfonic acid ester radical used as starting compounds in method (a) can be prepared by the process disclosed in DE-OS No. 2,735,110. The steroid-17$\alpha$,21-(dialkyl orthocarbonates) of the formula II to be used in method (b) are generally known compounds which can be prepared by the process described in German Patent Specification No. 1,668,079.

The steroid-21-alkyl- or -aryl-sulfonate-17-(alkyl carbonates) as well as the steroid-17$\alpha$,21-(dialkyl orthocarbonates) of the following 17,21-dihydroxy-steroids or corticoids can be used: cortisone, hydrocortisone, Reichstein's substance S, prednisone, prednisolone, 6$\alpha$-methylprednisolone, 16$\alpha$- and 16$\beta$-methylprednisolone, 9$\alpha$-fluoro- and 9$\alpha$-chloro-prednisolone, 16-methyleneprednisolone, 6$\alpha$,9$\alpha$-difluoroprednisolone, 6$\alpha$-methyl-9$\alpha$-fluoro-prednisolone, 6$\alpha$-fluoro-prednisolone, 9$\alpha$-fluoro-16$\alpha$-methyl-prednisolone, 9$\alpha$-fluoro-prednisolone, 9$\alpha$-fluoro-16$\alpha$-methyl-prednisolone, 9$\alpha$-fluoro-prednisolone, 9$\alpha$-fluoro-16$\alpha$-methyl-prednisolone, 6$\alpha$-fluoro-16$\alpha$-methyl-prednisolone, 6$\alpha$-fluoro-16$\beta$-methyl-prednisolone, 6$\alpha$-fluoro-16-methylene-prednisolone, 6$\alpha$,9$\alpha$-difluoro-16$\alpha$-methyl-prednisolone, 6$\alpha$,9$\alpha$-difluoro-16$\beta$-methyl-prednisolone, 6$\alpha$,9$\alpha$-difluoro-16- methylene-prednisolone, 9α-fluoro-6α,16α-dimethyl-prednisolone, 9α,16α-difluoro-prednisolone, 6α,9α-trifluoro-prednisolone, 17α,21-dihydroxy-Δ$^{4(5),9(11)}$-pregnadiene-dione(3,20), 17α,21-dihydroxy-9β-11β-oxido-Δ$^4$-pregnene-dione-(3,20), 17α,21-dihydroxy-9α,11β-dichloro-Δ$^{1,4}$-pregnadiene-dione-(3,20), 17α,21-dihydroxy-Δ$^{4(5),6(7)}$-pregnadiene-dione-(3,20), desoxycorticosterone, corticosterone, 16α-methyl-corticosterone, 9α-fluoro-16α-methyl-corticosterone, 6α,9α-difluoro-16α-methyl-corticosterone, 6α-fluoro-16α-methyl-corticosterone, 6,16α-2-dimethyl-4,6-pregnadiene-11β,17α,21-trione-[3,2-c]-2'-phenylpyrazole and -2'-p-fluorophenylpyrazole and corresponding compounds substituted in 9-position by fluorine. Still further, corticoids of the above designations can be used which carry, instead of a 6α-fluoro and/or 9α-fluoro and/or 11β-hydroxy substituent, a chloro-substituent oriented in the corresponding configuration. From among the aforesaid steroid-21-alkyl- or -aryl-sulfonate-17-(alkyl carbonate) the following compounds are preferred: 17-methyl-, 17-ethyl-, 17-n-propyl-, 17-n-butyl, and 17-n-pentyl carbonate as well as 21-methane-, 21-benzene-, 21-toluene, 21-p-chlorobenzene-, and 21-p-nitrobenzene-sulfonic acid ester. Preferred steroid-17,21-(dialkyl orthocarbonates) are 17,21-dimethyl-, 17,21-diethyl-, 17,21-di-n-propyl, 17,21-n-butyl and 17,21-n-pentyl carbonate.

The nucleophilic exchange of the 21-alkyl- or 21-arylsulfonic acid ester group for a halogen atom such as fluorine, chlorine, bromine or iodine of method (a) is carried out according to known methods. To this end, the steroid-21-sulfonic acid-17-(alkyl carbonate) is reacted at a temperature from 0° C. to the boiling point of the solvent used, preferably 70° C. to 120° C., for 1 minute to 7 days, preferably 0.5 to 16 hours, with a fluoride, chloride, bromide, or iodide of an alkali metal, alkaline earth metal or trialkylammonium, the alkali metal preferably being lithium, sodium or potassium, the alkaline earth metal preferably being magnesium or calcium and the trialkylammonium preferably being trimethyl-, triethyl-, tripropyl-, tributyl-ammonium, in an inert, preferably aprotic and polar solvent, for example acetone, ethylmethyl ketone, dimethyl formamide, N,N-dimethyl-acetamide, acetonitrile, N-methylpyrrolidone, hexamethyl-phosphoric acid triamide, dimethyl sulfoxide or optionally a mixture of the said solvents, under substantially anhydrous reaction conditions and isolated and purified in usual manner by pouring the reaction mixture into water optionally containing sodium chloride, filtering off the solid or oily precipitate, or extracting with a suitable organic solvent, washing with water, optionally distilling off the solvents and recrystallizing from a suitable solvent or solvent mixture.

According to an especially favorable and cautious embodiment of this method the cations of the aforesaid metal halides are transformed into a complex compound with a compound suitable for complex formation, preferably a "crown ether" (cryptate formation). The resulting increase of the degree of nucleophily of the respective halide ions makes possible an exchange of the sulfonate radical for the halogen even at a temperature of from 0° C. to 30° C. in a feasible and sufficient manner.

For this purpose, for example, the steroid-17-(alkyl carbonate)-21-sulfonic acid ester is dissolved in one of the aforesaid solvents or a solvent mixture, optionally with the addition of chlorinated hydrocarbons such as chloroform or methylene chloride, or non-chlorinated hydrocarbons such as benzene, toluene or cyclohexane, and the solution obtained is admixed with 1 to 3 molar equivalents of a cryptate solution prepared in known manner from one of the specified metal halides by reacting same with a crown ether (for example 18-crown-6) or a polyoxadiazamacrobicycle (for example Cryptofix ® 211 or 221 or 222) in the presence of one of the specified solvents, optionally while adding catalytic amounts of a low molecular weight alcohol, preferably methanol or ethanol, or with 1 to 5 molar equivalents of one of the specified metal halides with the addition of catalytic amounts of crown ether or polyoxadiazamacrobicycles of the above type (0.001 to 0.01 molar equivalent), allowed to react for 24 hours to 14 days, preferably 7 days, at a temperature of from 0° C. to 60° C., preferably room temperature, and the reaction mixture is worked up in the usual manner.

A similar strong acceleration of the nucleophilic exchange of the steroid-21-sulfonic acid ester group for one of the specified halide ions can be achieved by so-called "phase transfer catalysis". In this case, the nucleophilic exchange reaction takes place at the interface between an organic solvent or solvent mixture and an aqueous phase in the presence of catalytic amounts of quaternary ammonium or phosphonium salt or of a crown ether with addition of the halide ions to be introduced in the form of a salt.

To carry out this reaction the steroid-21-sulfonate, for example, is dissolved in one of the aforesaid solvents, preferably acrylonitrile or dimethyl sulfoxide, the solution of one of the aforesaid alkali metal or alkaline earth metal halides, for example potassium fluoride, potassium chloride, potassium bromide or potassium iodide, in water and 0.01 to 1 molar equivalent of a quaternary ammonium halide or ammonium sulfonate as catalyst, for example tricaprylmethyl-ammonium chloride, tri-n-octylmethyl-ammonium chloride, tributylhexadecyl-phosphonium iodide or bromide, or in its stead a crown ether, for example "[18]crown-6", is added as a catalyst. The reaction mixture is treated for 10 minutes to 100 hours, preferably 30 minutes to 48 hours, at a temperature from 0° C. to the boiling point of the reaction mixture, preferably 60° to 110° C.

The reaction mixture is then extracted one or several times in the usual manner, for example with a preferably-chlorinated organic solvent such as methylene chloride or chloroform, washed with water and the solvent is distilled off. The pure substance is obtained from the residue by working up in the usual manner.

According to method (b), the steroid-17-(alkyl carbonate)-21-halides of the invention can be produced from the basic steroid-17,21-(dialkyl orthocarbonates) by reacting the latter with an inorganic or organic acid halide compound donating halogen, for example a silyl halide, such as triethylsilyl or trimethylsilyl chloride, bromide, iodide or fluoride, or with a phosphorus acid or phosphorus acid halide, preferably phosphorus oxichloride, phosphorus tri- and phosphorus pentachloride or bromide, or with an acyl chloride, preferably acetyl and oxalyl chloride, or with a sulfonyl halide, preferably p-toluene-sulfonic acid chloride or methane-sulfonic acid chloride, or with an N-haloamide or imide, preferably N-chlorosuccinimide, N,N-dibromobenzene-sulfonamide, or with a triphenylalkyl halide, preferably triphenylmethyl chloride, in one of the aforesaid organic solvents or solvent mixtures, for 1 minutes to 60 hours, preferably 5 minutes to 24 hours, at a temperature from 0° C. to the boiling point of the solvent used, preferably at room temperature up to 120° C. In this reaction, the ring of 17,21-(dialkyl orthocarbonate) is opened in a manner such that the halogen takes the 21-position while the cyclic orthocarbonate opens to form the linear 17-(alkyl carbonate).

The steroid-17-(alkyl carbonate)-21-sulfonic acid esters or 21-ols to be used are obtained by the process described in DE-OS No. 2,735,110 and the basic steroid-17,21-(dialkyl orthocarbonates) can be prepared by the process disclosed in German Pat. No. 1,668,079.

The process products have valuable pharmacological properties. In the first place, they have a very strong local and topical antiphlogistic effect and the ratio of the local to the systemic antiphlogistic effect is favorable as can be deduced from standard pharmacological tests.

Owing to their very powerful local and topical antiphlogistic effect, the products of the process can be used with advantage in veterinary and human therapy in the form of suspensions, ointments, creams, solutions, sprays and the like, for the treatment of inflammatory dermatoses of very diverse cause. In the treatment of human beings and animals, preparations containing from 0.025 to 1% of the compounds of the invention are used. It is emphasized that it is especially advantageous for the local and topical form of therapy that the products, because of their favorable ratio of local to systemic antiphlogistic effect, may cause only slight systemic side effects even in the case of high dosage and long term therapy. In addition, the products have a significantly better stability to acids than the cyclic corticoid-17,21-orthocarbonates) from which they are derived. This fact is of decisive importance for a reliable therapeutical use of the claimed products.

The following examples illustrate the invention.

The melting points were determined in a Tottoli apparatus (Messrs. Büchi) and are not corrected.

The IR spectra (in KBr) were recorded using a Perkin-Elmer 521 grating spectrophotometer. In each case only the characteristic bands are given. The UV spectra (in methanol) were recorded using a Beckmann DK 1 A spectrophotometer. The investigations by mass spectroscopy (MS) were carried out using the MS 9 apparatus (Messrs. AEI).

Ready-to-use silica gel $F_{254}$ plates (Messrs. Merck) were used for thin layer chromatography (TLC).

Unless otherwise stated, the solvent used was methylene chloride:methanol = 19:1. In each case, developing was carried out once. The spots were rendered visible by spraying with 10% methanolic sulfuric acid and by heating to 100° C. The $R_f$ values are always to be understood as only relative values. Silica gel 60, particle size 0.063–0.2 mm (Messrs. Merck) was used for column chromatography.

EXAMPLE 1

(a) 2.2 g of dry lithium chloride are added to a solution of 1 g of prednisolone-17-(ethyl carbonate)-21-methanesulfonate in 20 ml of absolute dimethyl formamide and the mixture is stirred for 2 hours at 100° C. in a nitrogen atmosphere. After pouring off the reaction solution into approximately 150 ml of water containing sodium chloride, the mixture is exhaustively extracted with methylene chloride. The organic phase is washed with water, dried and freed from solvent by distillation in vacuo. 1.2 g of foam are obtained, which is subjected to chromatography on 30 g of silica gel with methylene chloride (dimensions of column 2.5×10 cm). The eluates, which show a substantially uniform $R_f$ value of 0.60 in the thin layer chromatogram, are combined and freed from solvent by distillation. The residue is recrystallized from methanol/diisopropyl ether, whereby 690 mg of 21-desoxy-prednisolone-17-(ethyl carbonate)-21-chloride melting at 167°–168° C. are obtained.

Characteristic IR bands 3520, 3430, 1740, 1725, 1650, 1270 cm$^{-1}$.

mass spectrum: M$^\oplus$=450.

TLC: $R_f$=0.60.

UV: λmax.=238 nm; ε=15,100.

Beilstein test: positive.

(b) The same product having the same data as indicated in Example 1(a) is obtained when, instead of prednisolone-17-(ethyl carbonate)-21-methanesulfonate, an equimolar amount of prednisolone-17-(ethyl carbonate)-21-toluenesulfonate or 21-p-chlorobenzenesulfonate is reacted and worked up under the conditions of Example 1(a).

EXAMPLE 2

When, in Example 1(a) or 1(b), instead of lithium chloride, an equimolar amount of lithium bromide is used and the mixture is reacted and worked up as described above, 490 mg of 21-desoxy-prednisolone-17-(ethyl carbonate)-21 bromide melting at 164° to 166° C. are obtained after crystallization from methanol/ether.

Characteristic IR band: 3440, 1730, 1655, 1610, 1270 cm$^{-1}$.

TLC: $R_f$=0.63.

UV: λmax.=238 nm; ε=14,750.

Beilstein test: positive.

EXAMPLE 3

460 mg of sodium iodide are added to a solution of 2.3 g of prednisolone-17-(ethyl carbonate)-21-p-chlorobenzenesulfonate in 46 ml of absolute ethylmethyl ketone. The mixture is refluxed for 2 hours (after about 30 minutes a precipitation is observed), then poured into 450 ml of water containing sodium chloride and exhaustively extracted with methylene chloride. After washing of the combined extracts with water, drying and removing the solvent by distillation, a foamy residue is obtained which is induced to crystallize with diethyl ether. 2.1 g of amorphous 21-desoxy-prednisolone-17-(ethyl carbonate)-21-iodide are obtained.

Characteristic IR bands: 3400, 1730, 1650, 1610, 1270 cm$^{-1}$.

UV: λmax.=238 nm; ε=15,150.

TLC: $R_f$=0.50, (eluent:toluene:methanol), (acetone=80:20:5).

analysis iodine: calc.: 23.4%, found: 21.6%.

EXAMPLE 4

21-Desoxy-21-fluoro-prednisolone-17-(ethyl carbonate)

1 g of prednisolone-17-(ethyl carbonate)-21-methanesulfonate is added to a suspension, previously stirred for 35 minutes at room temperature, of 145 mg of 18-crown-6 and 190 mg of potassium fluoride in 8 ml of acetonitrile. Stirring of the mixture is continued for 8 hours at 80° C. under N$_2$. After cooling, the reaction mixture is added while stirring to 50 ml of water and worked up as usual (extraction with methylene chloride, repeated washing with water, removal of solvent by distillation under reduced pressure, purification by chromatography as described in Example 1, recrystallization of the eluate residue (uniform in TLC) from methanol/diisopropyl ether). 310 g of 21-desoxy-21-fluoro-prednisolone-17-(ethyl carbonate) melting at 170° C. are obtained.

IR: 3520, 1735, 1720, 1650, 1270 cm$^{-1}$.
UV: $\lambda$max.=238 nm, $\epsilon$=1480.

Preparation of prednisolone-17-(ethyl carbonate)-21-p-chlorobenzenesulfonate 1.8 g of p-chlorobenzenesulfonic acid chloride are added at 0° C. to a solution of 3 g of prednisolone-17-(ethyl carbonate) in 35 ml of absolute acetone and 12 ml of absolute pyridine. After stirring for a period of 20 hours with gradually rising temperature from 0° C. to 22° C., the reaction mixture is poured into water, the precipitated oil is filtered off, taken up in methylene chloride, washed and the solvent is concentrated under reduced pressure. The residue is subjected to chromatography on silica gel (column 4×14 cm) using methylene chloride as eluant. The TLC pure fractions with $R_f$=0.60 are combined and crystallized from ethanol/ether. 2.6 g of prednisolone-17-(ethyl carbonate)-21-p-chlorobenzenesulfonate melting at 188° C. are obtained.

Mass spectrum: M+ =605.
IR: 3430, 3320, 1740, 1655, 1620, 1600, 1510, 1370, 1280, 1190, 1030 cm$^{-1}$.

EXAMPLE 5

(a) 2.2 g of dry lithium chloride are added to a solution of 1 g of prednisolone-17-(n-propyl carbonate)-21-methane-sulfonate in 20 ml of absolute dimethyl formamide and the mixture is stirred for 2 hours at 100° C. under nitrogen. The reaction solution is then poured into approximately 150 ml of water containing sodium chloride and the whole is exhaustively extracted with methylene chloride. The organic phase is washed with water, dried and the solvent is removed by distillation under reduced pressure. 1.2 g of a foam are obtained which is subjected to chromatography on 30 g of silica gel (dimensions of column 2.5×10 cm) using methylene chloride. The eluates substantially having a uniform $R_f$ value of 0.60 in the thin layer chromatogram are combined and freed from the solvent by distillation. The residue is recrystallized from methanol/diisopropyl ether. 710 g of 21-desoxy-prednisolone-17-(n-propyl carbonate)-21-chloride melting at 128° to 130° C. are obtained.

Characteristic IR bands: 3420, 1730, 1650, 1610, 1270-1280 cm$^{-1}$.
TLC: $R_f$=0.60.
UV: $\lambda$max.=238 nm; $\epsilon$=15,300.

(b) The same product having the data as indicated in Example 5(a) is obtained when, instead of prednisolone-17-(n-propyl carbonate)-21-methanesulfonate, an equimolar amount of prednisolone-17-(n-propyl carbonate)-21-toluenesulfonate or -21-n-chlorobenzenesulfonate is reacted and the reaction product is worked up under the conditions of Example 5(a).

EXAMPLE 6

When, in the reaction of Example 5(a) or 5(b), an equimolar amount of lithium bromide is used instead of lithium chloride, under otherwise identical conditions, and the reaction product is worked up as described and crystallized from methanol/ether, 490 g of 21-desoxy-prednisolone-17-(n-propyl carbonate)-21-bromide melting at 102° to 105° C. are obtained.

Characteristic IR bands: 3440, 1730, 1650, 1610, 1270 cm$^{-1}$.
TLC: $R_f$=0.63.
UV: $\lambda$max.=238 nm; $\epsilon$=14,900.

EXAMPLE 7

460 mg of sodium iodide are added to a solution of 2.3 g of prednisolone-17-(n-propyl carbonate)-21-p-chlorobenzenesulfonate in 46 ml of absolute ethylmethyl ketone. After a reflux period of 2 hours, the reaction mixture is added, while stirring, to 450 ml of water containing sodium chloride and extracted exhaustively with methylene chloride. The combined extracts are washed with water, dried and the solvent is distilled off, whereupon 2 g of a foamy residue are obtained which is 21-desoxy-prednisolone-17-(n-propyl carbonate)-21-iodide.

Characteristic IR bands: 3420, 1730, 1650, 1610, 1255 cm$^{-1}$.
Beilstein test: positive.
TLC: $R_f$=0.50, (eluent toluene:methanol), (acetone=80:20:5).
UV: $\lambda$max.=237 nm; $\epsilon$=13,800.

EXAMPLE 8

In the manner described in Example 4, 1 g of prednisolone-17-(n-propyl carbonate)-21-p-chlorobenzenesulfonate are reacted and worked up. 21-Desoxy-prednisolone-17-(n-propyl carbonate)-21-fluoride is obtained.

UV: $\lambda$max.=238 nm; $\epsilon$=13,900.

Preparation of prednisolone-17-(n-propyl carbonate)-21-p-chlorobenzenesulfonate 1.75 g of p-chlorobenzenesulfonic acid chloride are added dropwise at 0° C. to a solution of 3 g of prednisolone-17-(n-propyl carbonate) in 35 ml of absolute acetone and 12 ml of absolute pyridine. The reaction mixture is stirred for 20 hours with gradually rising temperature from 0° C. to 22° C., poured into water, extracted with methylene chloride, washed and the extraction agent is concentrated in vacuo. The residue is chromatographed on silica gel (column 4×14 cm) using methylene chloride as eluant. The TLC pure fractions of $R_f$ 0.60 are combined and crystallized from ethanol/ether.

2.5 g of prednisolone-17-(n-propyl carbonate)-21-p-chlorobenzenesulfonate melting at 105° C. are obtained.

Mass spectrum: M+ =620.
IR: 3430, 1730, 1655, 1610, 1600, 1350, 1265, 1170, 1030 cm$^{-1}$.

EXAMPLE 9

In the manner described in Example 1(a), 1 g of prednisolone-17-(n-butyl carbonate)-21-methanesulfonate are reacted with 2 g of lithium chloride and worked up. After crystallization from diisopropyl ether (rubbing), 670 mg of 21-desoxy-prednisolone-17-(n-butyl carbonate)-21-chloride melting at 151° to 155° C. are obtained.

Characteristic IR bands: 3430, 1740, 1660, 1610, 1270 cm$^{-1}$.
UV: $\lambda$max.=238 nm; $\epsilon$=14,750.
Beilstein test: positive.

EXAMPLE 10

1 g of prednisolone-17-(n-butyl carbonate)-21-methanesulfonate are reacted with 4.5 g of lithium bromide and worked up in the manner described in Example 1(a). After adding some diisopropyl ether, 685 mg of 21-desoxy-prednisolone-17-(n-butyl carbonate)-21-bromide melting at about 140° C. with decomposition are obtained.

UV: λmax.=238 nm; ε=15,200.
Beilstein test: positive.

EXAMPLE 11

2.3 g of prednisolone-17-(n-butyl carbonate)-21-p-chlorobenzenesulfonate are reacted with 460 mg of sodium iodide and the reaction product is worked up as described in Example 3. After adding some ether, 2.3 g of 21-desoxy-prednisolone-17-(n-butyl carbonate)-21-iodide melting at about 100° C. with decomposition are obtained.

UV: λmax.=237 nm; ε=13,600.
Beilstein test: positive.

When 1 g of prednisolone-17-(n-butyl carbonate)-21-p-chlorobenzenesulfonate is reacted with potassium fluoride and the reaction product is worked up as described in Example 4, 21-desoxy-prednisolone-17-(n-butyl carbonate)-21-fluoride is obtained.

UV: λmax.=238 nm; ε=14,400.

Prednisolone-17-(n-butyl-carbonate)-21-p-chlorobenzenesulfonate is prepared from prednisolone-17-(n-butyl carbonate) and -p-chlorobenzenesulfonic acid chloride in the same manner as described in the second part of Example 4 for the manufacture of prednisolone-17-(ethyl carbonate)-21-p-chlorobenzenesulfonate.

EXAMPLE 12

1 g of prednisolone-17-(n-butyl carbonate)-21-p-chlorobenzenesulfonate are reacted and the reaction product is worked up in the same manner as described in Example 4. 21-Desoxy-prednisolone-17-(n-butyl carbonate)-21-fluoride is obtained.

UV: λmax.=238 nm; ε=14,400.

Prednisolone-17-(n-butyl carbonate)-21-p-chlorobenzenesulfonate is prepared from prednisolone-17-(n-butyl carbonate) and p-chlorobenzenesulfonic acid chloride in the same manner as described in the second part of Example 4 for the manufacture of prednisolone-17-(ethyl carbonate)-21-p-chlorobenzenesulfonate.

EXAMPLE 13

1 g of prednisolone-17-(n-pentyl carbonate)-21-methanesulfonate is reacted with 2 g of lithium chloride and the reaction product is worked up as described in Example 1(a). After crystallization from diisopropyl ether (rubbing), 540 mg of 21-desoxy-prednisolone-17-(n-butyl carbonate) melting at 118° to 124° C. are obtained.

Characteristic IR bands: 3430, 1740, 1660, 1610, 1270 cm$^{-1}$.
UV: λ238 nm, ε=14,400.
Beilstein test: positive.

EXAMPLE 14

1 g of prednisolone-17-(n-pentyl carbonate)-21-methanesulfonate is reacted with 4.5 g of lithium bromide and the reaction product is worked up as described in Example 1(a). After adding some diisopropyl ether, 525 mg of desoxy-prednisolone-17-(n-pentyl carbonate)-21-bromide melting at about 100° C. with decomposition are obtained.

UV: λmax.=238 nm; ε=14,800.
Beilstein test: positive.

EXAMPLE 15

2.3 g of prednisolone-17-(n-pentyl carbonate)-21-p-chlorobenzenesulfonate are reacted with 460 g of sodium iodide and the reaction product is worked up as described in Example 3. After digestion with ether, 2.0 g of amorphous 21-desoxy-prednisolone-17-(n-pentyl carbonate)-21-iodide are obtained.

UV: λmax.=238 nm; ε=13,000.
Beilstein test: positive.

EXAMPLE 16

1 g of prednisolone-17-(n-pentyl carbonate) -21-p-chlorobenzenesulfonate is reacted and the reaction product worked up as described in Example 4. 21-Desoxy-prednisolone-17-(n-pentyl carbonate)-21-fluoride is obtained.

UV: λmax.=238 nm; ε=14,100.

Prednisolone-17-(n-pentyl carbonate)-21-p-chlorobenzene-sulfonate is prepared from prednisolone-17-(n-pentyl carbonate) and p-chlorobenzenesulfonic acid chloride in the same manner as described for the manufacture of prednisolone-17-(ethyl carbonate)-21-p-chlorobenzenesulfonate in the second part of Example 4.

EXAMPLE 17

(a) 2.2 g of dry lithium chloride are added to a solution of 1 g of dexamethasone-17-(ethyl carbonate)-21-p-chlorobenzenesulfonate in 20 ml of absolute dimethyl formamide and the mixture is stirred for 2 hours at 100° C. under nitrogen. The reaction mixture is then poured into approximately 100 ml of water containing sodium chloride and exhaustively extracted with methylene chloride. The organic phase is washed with water, dried and freed from solvent by distillation in vacuo. 1.0 g of a foam is obtained which is chromatographed on 30 g of silica gel (dimensions of column 2.5×10 cm) using methylene chloride. The eluates having a substantially uniform $R_f$ value≈0.60 in thin layer chromatography are combined and freed from solvent by distillation. The residue is recrystallized from methanol/diisopropyl ether. 620 g of 21-desoxydexamethasone-17-(ethyl carbonate)-21-chloride melting at 222° C. are obtained. When the reaction product is not recrystallized but digested with diisopropyl ether only, the melting point is generally in the range of from 140° to 145° C.

Characteristic IR bands: 3420, 1730, 1655, 1600, 1260 cm$^{-1}$.

mass spectrum: M$^{\oplus}$=482.
TLC: $R_f$=0.35 (ethyl acetate/toluene 1:1).
UV: λmax.=238 nm, ε=15,000.

(b) The same product having the same data as indicated in Example 17(a) is obtained by reacting, instead of dexamethasone-17-(ethyl carbonate)-21-p-chlorobenzenesulfonate, an equimolar amount of dexamethasone-17-(ethyl carbonate)-21-toluenesulfonate or 21-methanesulfonate and working up as described above.

EXAMPLE 18

When an equimolar amount of lithium bromide is used instead of lithium chloride in Example 17(a) and 17(b) and the reaction is carried out in the same manner (with the exception that the reaction lasts for 3.5 hours instead of 2 hours), the reaction mixture is poured into water, the precipitate is filtered off, washed with water and dried over phosphorus pentoxide under high vacuum, at 70° C., 710 mg of 21-desoxy-dexamethasone-17-(ethyl carbonate)-21-bromide melting at 165° C. are obtained.

IR bands: 3430, 1725, 1655, 1610, 1270 cm$^{-1}$.
TLC: $R_f=0.32$ (toluene/ethyl acetate 55:45).
mass spectrum: M$^+=416$.
Beilstein test: positive.
UV: $\lambda$max. $=238$ nm; $\epsilon=15,400$.

EXAMPLE 19

800 mg of sodium iodide are added to a solution of 2.3 g of dexamethasone-17-(ethyl carbonate)-21-p-chlorobenzenesulfonate in 46 ml of absolute ethylmethyl ketone. The mixture is refluxed for 2 hours and then added while stirring to 450 ml of water containing sodium chloride. The precipitate formed is filtered off, washed with water, and dried in vacuo over P$_2$O$_5$ and digested with diethyl ether. 2.1 g of 21-desoxy-dexamethasone-17-(ethyl carbonate)-21-iodide are obtained.

Characteristic IR bands: 3420, 1730, 1660, 1610, 1270 cm$^{-1}$.
TLC: $R_f=0.50$ (eluent toluene:methanol:acetone 80:20:5).
Beilstein test: positive.
UV: $\lambda$max. $=237$ nm; $\epsilon=14,600$.

EXAMPLE 20

In the manner described in Example 4, 1 g of dexamethasone-17-(ethyl carbonate)-21-p-chlorobenzenesulfonate are reacted and the reaction product is worked up, whereby the 21-desoxydexamethasone-17-(ethyl carbonate)-21-fluoride is obtained.
UV: $\lambda$max. $=238$ nm; $\epsilon=14,600$.

Preparation of dexamethasone-17-(ethyl carbonate)-21-p-chlorobenzenesulfonate 1.8 g of p-chlorobenzenesulfonic acid chloride are added at 0° C. to a solution of 3 g of dexamethasone-17-(ethyl carbonate) in 35 ml of absolute acetone and 12 ml of absolute pyridine. The mixture is stirred for 20 hours with gradually rising temperature from 0° to 22° C., poured into water, the precipitated oil is filtered off, taken up in methylene chloride, washed and the solvent is concentrated in vacuo. The residue is rubbed with diisopropyl ether, whereupon 3.8 g of dexamethasone-17-(ethyl carbonate)-21-p-chlorobenzenesulfonate melting at 123° C. (with foaming) are obtained.

Mass spectrum: M$^+=638$.
IR: 3430, 1730, 1655, 1620, 1600, 1370, 1260, 1180 cm$^{-1}$.
UV: $\lambda$max. $=232$ nm; $\epsilon=24,500$.

EXAMPLE 21

21-Desoxy-21-chlorodexamethasone-17-(propyl carbonate (a) Dexamethasone-17-(propyl carbonate)-21-methanesulfonate 46.8 g of dexamethasone-17-(propyl carbonate) are dissolved in a mixture of 470 ml of acetone and 173 ml of pyridine. After cooling to 0° C., 33 ml of mesyl chloride are added dropwise while stirring. Stirring is continued is continued for 5½ hours at 0° to 5° C., whereupon the mixture is poured into approximately 4 liters of water. The mixture is left to stand for a little while, the precipitate formed is filtered off with suction and taken up in methylene chloride. After washing with water and drying over sodium sulfate, the methylene chloride extract is concentrated to dryness in vacuo. The distillation residue is recrystallized from toluene/diisopropyl ether. 49.3 g of dexamethasone-17-(propyl carbonate)-21-methane-sulfonate melting at 161° to 163° C. are obtained.

(b) 40.0 g of dexamethasone-17-(propyl carbonate)-21-methanesulfonate are added to a mixture of 400 ml of absolute dimethyl formamide and 80.0 g of lithium chloride dried in vacuo at 120° C. The reaction mixture is stirred for 6 hours under nitrogen at an internal temperature of 100° C. Next, it is evaporated to dryness in vacuo at an external temperature of about 50° C. The residue is stirred with a mixture of 100 ml of toluene and 100 ml of ethyl acetate and, to remove the lithium salts, 200 ml of water is added. After separation of the aqueous phase and drying, the mixture is again concentrated and, to remove sparingly soluble constituents, the residue is digested with toluene in ethyl acetate. The mother liquors are evaporated in a rotary evaporator and the residue is subjected to chromatography on a column of 1.6 kg of silica gel using toluene/ethyl acetate 4:1 as eluent. Control of thin layer chromatography is carried out with authentic material using toluene/ethyl acetate 65:35 as eluant. After recrystallization from ethyl acetate and then from ethanol, 10.2 g of 21-desoxy-dexamethasone-17-(propyl carbonate)-21-chloride melting at 189°–190° C. are obtained.

EXAMPLE 22

21-Desoxy-urbasone-17-(propyl carbonate)-21-chloride 1.1 g of urbasone-17-(propyl carbonate) are dissolved in 4 ml of absolute piperidine and 1 ml of mesyl chloride is added while stirring at 0° C. Stirring is continued for 1 hour at room temperature. Next, the reaction mixture is added while stirring to approximately 50 ml of ice-cold 1 N hydrochloric acid. The precipitate formed is filtered off with suction, washed with water, dried in vacuo over calcium chloride and recrystallized at 30° to 40° C. from methanol and a little ether. 1.21 g of urbasone-17-(propyl carbonate)-21-methanesulfonate melting at 143° to 145° C. are obtained.

1.0 g of urbasone-17-(propyl carbonate)-21-mesylate is dissolved in 20 ml of absolute dimethyl formamide, 2 g of anhydrous lithium chloride are added and the mixture is stirred for 4 hours under nitrogen at an internal temperature of 95° C. Next, the reaction mixture is added while stirring to 100 ml of cold water, the precipitate formed is filtered off with suction and washed with a small amount of water. The filter residue is taken up in methylene chloride, washed again with water, dried over sodium sulfate, concentrated in vacuo to a small volume and chromatographed on a column of 50 g of silica gel using toluene/ethyl acetate as eluant. After recrystallization under the conditions of Example 1(b) from methylene chloride/hexane, 380 mg of 21-desoxy-urbasone-17-(propyl carbonate)-21-chloride melting at 117° to 120° C. are obtained.

EXAMPLE 23

16α-Methyl-21-desoxy-prednisolone-17-(n-propyl carbonate) 9α,21-dichloride 0.544 g of 9α-chloro-16α-methyl-prednisolone-17-(n-propyl carbonate) is dissolved in 2 ml of absolute pyridine and 0.5 ml of methanesulfonic acid chloride is added at 0° C. Stirring of the mixture is continued for 30 minutes at room temperature, whereupon the reaction mixture is added while stirring to 25 ml of ice-cold 1 N hydrochloric acid. The precipitate formed is filtered off with suction, washed with water and recrystallized from methanol. 470 mg of 9α-chloro-16α-methyl-prednisolone-17-(n-propyl carbonate)-21-methanesulfonate melting at 203° to 204° C. are obtained. 200 mg of the 21-methanesulfonate are dissolved in 4 ml of absolute dimethyl formamide. After addition of 400 mg of dry lithium bromide, the mixture is stirred for 6 hours at 100° C. under nitrogen. The reaction mixture is then added while stirring to 25 ml of water, the precipitate formed is filtered off with suction, taken up in methylene chloride and washed with a small amount of water. After drying over sodium sulfate, the mixture is evaporated to dryness in vacuo and the distillation residue is dissolved in a very small amount of methylene chloride, charged to a column of 20 g of silica gel and chromatographed using methylene chloride as eluant with TLC-control as in Example 21. The authentic fractions are collected and concentrated in vacuo. After recrystallization from diisopropyl ether/petroleum ether, 115 mg of 16α-methyl-21-desoxy-prednisolone-17-(n-propyl carbonate)-9α,21-dichloride melting at 193° to 196° C. are obtained.

9α-Chloro-16α-methyl-prednisolone-17-(n-propyl carbonate) used as starting compound can be prepared as described in DE-AS No. 1,668,079. According to a preferred process, 3.3 g of 9α-chloro-16α-methyl-prednisolone are dissolved in 97 ml of absolute dioxane and, after the addition of 3.5 g of tetrapropyl orthocarbonate and 190 mg of p-toluenesulfonic acid, the mixture is stirred for 4 hours at room temperature. The reaction mixture is then added to approximately 500 ml of about 1% aqueous sodium bicarbonate solution. The precipitate formed is filtered off with suction and recrystallized from ethanol/petroleum ether. It is dissolved in a small amount of methylene chloride containing 1% of methanol and chromatographed on 20 g of silica gel using the same solvent mixture as eluent. With control of the individual fractions by thin layer chromatography, 2.68 g of 9α-chloro-16α-methyl-prednisolone-17,21-(dipropyl orthocarbonate) melting at 222° to 225° C. are obtained.

2.5 g of the orthocarbonate obtained are added to 136 ml of glacial acetic acid containing 0.61 ml of water and the mixture is stirred for 4 hours at room temperature. The mixture is then added while stirring to 500 ml of sodium chloride solution and the precipitate formed is filtered off with suction, washed with a small amount of water and dried at 80° C. in a high vacuum. 2.2 g of 9α-chloro-16α-methyl-prednisolone-17-(n-propyl carbonate) melting at 230° to 235° C. are obtained, which has a sufficient purity for further reactions.

EXAMPLE 24

6α-Methyl-21-desoxy-21-chloro-prednisolone-17-(propyl carbonate)

1 g of urbasone-17-(propyl carbonate)-21-methanesulfonate are dissolved in 27 ml of acetone and, at 0° C. and under nitrogen while stirring, 0.7 ml of a $CrO_3$ solution according to Jones (prepared by dissolving 6.67 g of chromium trioxide in a mixture of 25 ml of water and 5.33 ml of concentrated sulfuric acid) is added dropwise.

Stirring of the mixture is continued for 2 hours at 0° C. and for another hour at room temperature, whereupon the reaction mixture is extracted with a mixture of diisopropyl ether and ethyl acetate, the organic phase is thoroughly washed with water and dried over sodium sulfate. After concentration in vacuo, the resulting oil is caused to crystallize with diisopropyl ether. 0.78 g of 6α-methyl-prednisolone-17-(propyl carbonate)-21-methanesulfonate melting at 92° to 95° C. are obtained.

700 mg of the compound obtained are added to a mixture of 7 ml of absolute dimethyl sulfonamide and 1.4 g of dry lithium chloride, with careful exclusion of humidity, and the mixture is stirred for 4 hours under dry nitrogen and at 90° C. The product is worked up as described in Example 1 (chromatography on 30 g of silica gel). 175 mg of 6α-methyl-21-desoxy-21-chloro-prednisolone-17-(propyl carbonate) melting at 123° to 126° C. are obtained.

EXAMPLE 25

9α-Fluoro-16α-methyl-21-desoxy-21-chloro-prednisone-17-(propyl carbonate)

2.7 g of dexamethasone-17-(propyl carbonate)-21-methanesulfonate (Example 21), dissolved in 81 ml of acetone, are treated as described in Example 24 with 2.16 ml of Jones reagent. After the usual working up, 2.27 g of 9α-fluoro-16α-methyl-prednisone-17-(propyl carbonate)-21-methanesulfonate melting at 100° to 105° C. with decomposition are obtained.

1.5 g of this compound are dissolved in a mixture of 55 ml of anhydrous acetone and 34 ml of dry dimethyl formamide and, after addition of 3 g of dry lithium chloride, the mixture is refluxed for 6 hours while stirring. It is then concentrated under nitrogen in vacuo to about ⅓ of its volume and worked up as described in Example 3.

840 mg of 9α-fluoro-16α-methyl-21-desoxy-21-chloroprednisone-17-(propyl carbonate) melting at 152° to 155° C. are obtained.

EXAMPLE 26

(a) In the manner described in Example 17(a), 1 g of dexamethasone-17-(n-butyl carbonate)-21-p-chlorobenzenesulfonate are reacted with 2 g of lithium chloride and the reaction product is worked up. After crystallization from diisopropyl ether (rubbing), 600 mg of 21-desoxydexamethasone-17-(n-butyl carbonate)-21-chloride melting at 136° C. are obtained.

Characteristic IR bands: 3430, 1730, 1660, 1610, 1260–1280 $cm^{-1}$.

UV: λmax. =238 nm; ε=15,200.

Mass spectrum: M+ =510.

(b) In the manner described in Example 17(a), 1 g of dexamethasone-17-(n-butyl carbonate)-21-methanesulfonate is reacted with 4.5 g of lithium bromide and the reaction product is worked up. After adding some diisopropyl ether, 585 mg of 21-desoxy-dexamethasone-17-(n-butyl carbonate)-21-bromide melting at 120° to 125° C. with decomposition are obtained.

UV: λmax. =238 nm; ε=14,750.

EXAMPLE 27

In the manner described in Example 19, 2.3 g of dexamethasone-17-(n-butyl carbonate)-21-p-chlorobenzenesulfonate are reacted with 460 mg of sodium iodide and the reaction product is worked up. After adding some ether, 2.0 g of 21-desoxy-dexamethasone-17-(n-butyl carbonate)-21-iodide are obtained.

UV: λmax. =238 nm; ε=13,600.
Beilstein test: positive.

Dexamethasone-17-(n-butyl carbonate)-21-p-chlorobenzenesulfonate is prepared from dexamethasone-17-(n-butyl carbonate) and p-chlorobenzenesulfonic acid chloride as described in the second part of Example 4 for the manufacture of prednisolone-17-(ethyl carbonate)-21-p-chlorobenzenesulfonate.

IR: 3430, 1730, 1660, 1610, 1600, 1370, 1270, 1180 cm$^{-1}$.
UV: λmax. =231 nm; ε=23,700.

EXAMPLE 28

In the manner described in Example 17(a), 1 g of dexamethasone-17-(n-pentyl carbonate)-21-methanesulfonate are reacted with 2 g of lithium chloride and the reaction product is worked up. After recrystallization from diisopropyl ether and cyclohexane (rubbing), 480 g of amorphous 21-desoxy-dexamethasone-17-(n-butyl carbonate)-21-chloride are obtained.

Characteristic IR bands: 3430, 1740, 1660, 1610, 1270 cm$^{-1}$.
UV: λmax. =238 nm; ε=13,600.
Beilstein test: positive.

EXAMPLE 29

In the manner described in Example 17(a) 1 g of dexamethasone-17-(n-pentyl carbonate)-21-methanesulfonate are reacted with 4.5 g of lithium bromide and the reaction product is worked up. After adding some diisopropyl ether/hexane, 520 g mg of amorphous desoxy-dexamethasone-17-(n-pentyl carbonate)-21-bromide are obtained.

UV: λmax. =238 nm; ε=13,400.
Beilstein test: positive.

EXAMPLE 30

In the manner described in Example 19, 2.3 g of dexamethasone-17-(n-pentyl carbonate)-21-p-chlorobenzenesulfonate are reacted with 460 mg of sodium iodide and the reaction product is worked up. After digesting with diisopropyl ether, 2.0 g of amorphous 21-desoxy-dexamethasone-17-(n-pentyl carbonate)-21-iodide are obtained.

UV: λmax. =238 nm; ε=12,800.
Beilstein test: positive.

Dexamethasone-17-(n-pentyl carbonate)-21-p-chlorobenzenesulfonate is prepared from dexamethasone-17-(n-pentyl carbonate) and p-chlorobenzenesulfonic acid chloride in the same manner as described in the second part of Example 4 for the manufacture of prednisolone-17-(ethyl carbonate)-21-p-chlorobenzenesulfonate.

EXAMPLE 31

(a) 22 g of dry lithium chloride are added to a solution of 10 g of dexamethasone-17-(n-propyl carbonate)-21-p-chlorobenzenesulfonate in 200 ml of absolute dimethyl formamide and the mixture is stirred for 30 minutes to 1 hour at 100° C. under nitrogen. Next, the reaction solution is poured into approximately 1 liter of water containing sodium chloride, the precipitate formed is filtered off, washed with water and dried in vacuo over P$_2$O$_5$. The dry precipitate (7.4 g) is chromatographed on 500 g of silica gel (dimensions of column 4.5×70 cm) using toluene/ethyl acetae ≈4:1. The eluates showing a substantially uniform R$_f$ value of ≈0.60 in the thin layer chromatogram are combined and freed from solvent by distillation. The residue is recrystallized from methanol/diisoproypl ether. 5.2 g of 21-desoxy-dexamethasone-17-(n-propyl carbonate)-21-chloride melting at 190° C. are obtained.

Characteristic IR bands: 3430, 1730, 1655, 1610, 1285, 1260 cm$^{-1}$.
mass spectrum: M$^{\oplus}$=496.
TLC: R$_f$≈0.63, (no side spots).
UV: λmax.=239 nm; ε=15,600.

(b) The same product having the same data as specified in Example 31(a) is obtained by reacting, instead of dexamethasone-17-(n-propyl carbonate)-21-p-chlorobenzenesulfonate, an equimolar amount of dexamethasone-17-(n-propyl carbonate)-21-toluenesulfonate and working up as described above.

EXAMPLE 32

When, in the reaction of Example 31(a) instead of lithium chloride, an equimolar amount of lithium bromide is used and the reaction is carried out as described in that example, the reaction mixture is poured into water and the precipitate is dried over phosphorus pentoxide under a high vacuum at 70° C., 4.8 g of 21-desoxy-dexamethasone-17-(n-propyl carbonate)-21-bromide are obtained melting at 175° to 180° C.

IR bands: 3430, 1730, 1660, 1610, 1270 cm$^{-1}$.
UV: λmax.=238 nm; ε=15,700.
Beilstein test: positive.

EXAMPLE 33

800 mg of sodium iodide are added to a solution of 2.3 g of dexamethasone-17-(n-propyl carbonate)-21-p-chlorobenzenesulfonate in 46 ml of absolute ethylmethyl ketone. The mixture is refluxed for 2 hours, stirred into 450 ml of water containing sodium chloride and the precipitate formed is filtered off. After washing with water, drying in vacuo over P$_2$O$_5$, the precipitate is digested with diethyl ether. 2.0 g of 21-desoxy-dexamethasone-17-(n-propyl carbonate)-21-iodide are obtained.

Characteristic IR bands: 3420, 1730, 1660, 1610, 1270 cm$^{-1}$.
TLC: R$_f$≈0.50. (eluant: toluene:methanol:acetone=80:20:5).
UV: λmax.=238 nm; ε=14,900.
Beilstein test: positive.

EXAMPLE 34

In the manner described in Example 4, 1 g of dexamethasone-17-(n-propyl carbonate)-21-p-chlorobenzenesulfonate are reacted and the reaction product is worked up. 21-Desoxy-dexamethasone-17-(n-propyl carbonate)-21-fluoride is obtained.

UV: λmax.=238 nm; ε=15,100.

Preparation of dexamethasone-17-(n-propyl carbonate)-21-p-chlorobenzenesulfonate 2.6 g of p-chlorobenzenesulfonic acid chloride are added at 0° C. to a solution of 3 g of dexamethasone-17-(n-propyl carbonate) in 35 ml of absolute acetone and 12 ml of absolute pryidine. The mixture is stirred for 20 hours with gradually rising temperature from 0° to 22° C. and poured into water. The precipitated oil is filtered off, taken up in methylene chloride and washed, and the solvent is evaporated in vacuo. 3.8 g of dexamethasone-17-(n-propyl carbonate)-21-p-chlorobenzenesulfonate having a softening point of 87° C. are obtained in the form of a foam.

Mass spectrum: $M^\oplus = 652$.

IR: 3430, 1730, 1660, 1620-1600, 1370, 1260, 1180 $cm^{-1}$.

UV: $\lambda max. = 232$ nm; $\epsilon = 27,900$.

EXAMPLE 35

21-Desoxy-21-fluoro-dexamethasone-17-(ethyl carbonate)

(a) 0.7 ml of trimethylsilyl fluoride is added to a solution of 0.5 g of dexamethasone-17,21-(diethyl orthocarbonate) in 5 ml of absolute dimethyl formamide and the mixture is stirred for 3 hours at 25° C. It is then poured into 30 ml of water, while stirring, and extracted with methylene chloride. The combined methylene extracts are repeatedly washed with water and the organic phase is concentrated to dryness in vacuo. The distillation residue is dissolved in a very small amount of methylene chloride and the solution is chromatographed on a column of 20 g of silica gel using methylene chloride as eluant under the usual conditions. After recrystallization from acetone/hexane, 160 mg of 21-desoxy-21-fluoro-dexamethasone-17-(ethyl carbonate) melting at 167° to 170° C. are obtained.

(b) 500 mg of dexamethasone-17-(ethyl carbonate)-21-methanesulfonate are added to a suspension, which has previously been stirred for 35 minutes at room temperature, of 73 mg of 18-crown-6 and 95 mg of potassium fluoride in 4 ml of acetonitrile. The whole is stirred for 8 hours at 80° C. under nitrogen. After cooling, the reaction mixture is added while stirring to 20 ml of water and worked up as described sub (a). 140 mg of 21-desoxy-21-fluoro-dexamethasone-17-(ethyl carbonate), which is identical with the product under (a), are obtained.

EXAMPLE 36

In the process described in Example 17(a), instead of dexamethasone-17-(ethyl carbonate)-21-p-chlorobenzenesulfonate, the 17-ethyl carbonate or the 17-n-propyl carbonate or the 17-n-butyl carbonate or prednisone-, cortisole-, cortisone-, 6α-methyl-prednisolone-, betamethasone-, beclomethasone-, 6α-fluoro-dexamethasone-, 6,10α-2-dimethyl-4,6-pregnadiene-11β, 17α,21-triol-3,2-c-2-phenylpyrazole (bimedrazol)-, 6α-fluoro-prednisolone-, 16α- or 16β-methyl-prednisolone-, 6α,16α- or β-dimethyl-prednisolone- or 9α-chloro-prednisolone-21-p-chlorobenzene sulfonate is reacted and the reaction product is worked up and isolated as described in said example, the corresponding 21-chloro-21-desoxy-17-(alkyl carbonate)-corticoids of the indicated corticosteroids are obtained.

EXAMPLE 37

When in Example 18, instead of dexamethasone-17-(ethyl carbonate)-21-p-chlorobenzenesulfonate, the 17-ethyl carbonate or the 17-n-propyl carbonate or the 17-n-butyl carbonate of prednisone-, cortisole-, cortisone-, 6α-methyl-prednisolone-, betamethasone-, beclomethasone-, 6α-fluoro-dexamethasone-, 6,16α-2-dimethyl-4,6-pregnadiene-11β, 17α,21-triol-3,2-c-2-phenylpyrazole (bimedrazol)-, 6α-fluoro-prednisolone-, 16α- or 16β-methyl-prednisolone-, 6α,16α- or β-dimethyl-prednisolone- or 9α-chloro-prednisolone-21-p-chlorobenzenesulfonate is reacted and the reaction product is worked up and isolated as indicated in said example, the corresponding 21-bromo-21-desoxy-17-(alkyl carbonate) corticoid of the indicated corticosteroids are obtained.

EXAMPLE 38

When in Example 19, instead of dexamethansone-17-(ethyl carbonate)-21-p-chlorobenzenesulfonate, the 17-ethyl carbonate or the 17-n-propyl carbonate or the 17-n-butyl carbonate of prednisone-, cortisole-, cortisone-, 6α-methyl-prednisolone-, betamethasone, beclomethasone-, 6α-fluoro-dexamethasone-, 6,16α-2-dimethyl-4,6-pregnadiene-11β,17,21-triol-3,2-c-2-phenylpyrazole (bimedrazol)-, 6α-fluoro-prednisolone-, 16α- or 16β-methyl-prednisolone-, 6α,16α- or β-dimethyl-prednisolone- or 9α-chloro-prednisolone-21-p-chlorobenzenesulfonate is reacted and the reaction product is worked up and isolated as indicated in said example, the corresponding 21-iodo-21-desoxy-17-(alkyl carbonate)-corticords of the indicated corticosteroids are obtained.

EXAMPLE 39

21-Desoxy-21-chloro-dexamethasone-17-(ethyl carbonate) and analogs thereof 1 ml of trimethylsilyl chloride is added to a solution of 0.5 g of dexamethasone-17,21-(diethyl orthocarbonate) in 5 ml of absolute dimethyl formamide or acetonitrile and the mixture is stirred for 16 hours at 25° C. It is then added to 30 ml of water while stirring and extracted with methylene chloride. After repeated washing of the combined methylene chloride extracts with water, the organic phase is concentrated to dryness in vacuo. The distillation residue is dissolved in a very small amount of methylene chloride and chromatographed as usual on a column of 20 g of silica gel using methylene chloride as eluant. After recrystallization from acetone/hexane, 170 mg of 21-desoxy-21-chloro-dexamethasone-17-(ethyl carbonate) having the same data as the compound of Example 17(a) are obtained.

When the reaction is carried out with a corresponding amount of dexamethasone-17,21-(di-n-propyl orthocarbonate) and trimethylsilyl chloride and the reaction product is worked up as described above, 21-desoxy-21-chlorodexamethasone-17-(n-propyl carbonate) having the same melting point as the product of Example 21(b) is obtained after crystallization.

When the reaction is carried out in the same manner but with the use, instead of the dexamethasone-17,21-(dialkyl orthocarbonates), of 0.5 g of prednisolone-17,21-(diethyl carbonate) or (di-n-propyl carbonate), the 21-desoxy-21-chloro-prednisolone-17-(ethyl carbonate) or (n-propyl carbonate) is obtained after working up and isolation, all data of which are exactly the same as those of the products obtained according to Example 1 and Example 5(a).

EXAMPLE 40

2 ml of a $CrO_3$ oxidation solution (prepared by dissolving 13.36 g of $CrO_3$ in 30 ml of water, adding dropwise 11.5 ml of concentrated sulfuric acid while cooling with ice and making up to 50 ml) are added dropwise at 0° C. while stirring to a solution of 2.5 g of 21-desoxy-dexamethasone-17-(ethyl carbonate)-21-chloride, prepared as described in Example 17(a) in 75 ml of acetone for analysis. The mixture is stirred for 1 hour at 0° C. and for 1.5 hours at 20° C. and then poured into water containing pyridine in an amount necessary for neutralization. The reaction mixture is repeatedly extracted with methylene chloride, washed with water, dried and concentrated in vacuo. The foam obtained is recrystallized from acetone/diisopropyl ether. 2.0 g of 21-desoxy-11-dehydro-dexamethasone-17-(ethyl carbonate)-21-chloride melting at 214° C. are obtained.

IR: 1720-1740, 1660, 1625, 1280, 1260 cm$^{-1}$, no more band in the range near 3420 cm$^{-1}$ (OH).

UV: λmax.=238 nm; ε=15,200.

When, instead of 21-desoxy-11-dehydro-dexamethasone-17-(ethyl carbonate)-21-chloride, the corticoid-17-(alkyl carbonates) prepared as described in the preceding examples and having a hydroxy group in 11-position and a halogen atom (F, Cl, Br, I) or an alkyl- or aryl-sulfonic acid ester group in 21-position are used in the aforesaid reaction, the 11-dehydro derivatives of the corresponding 21-desoxy-corticoid-17-(alkyl carbonate)-21-halides or -21-alkylsulfonic acid esters or -21-arylsulfonic acid esters are obtained.

What is claimed is:

1. A corticoid-21-chloro-17-(alkyl carbonate) selected from the group consisting of compounds of the formula

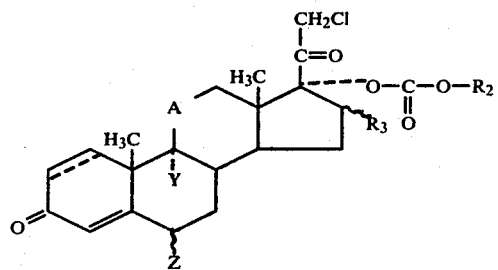

wherein A is

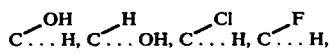

or C=O, and compounds of the formula

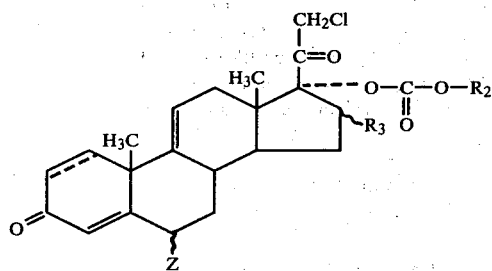

wherein
Y is hydrogen, fluorine, or chlorine;
Z is hydrogen, chlorine, fluorine, or methyl;
$R_3$ is hydrogen, α-methyl, or β-methyl; and
$R_2$ is alkyl having 1 to 10 carbon atoms.

2. A compound as in claim 1 wherein A is C=O.

3. A compound as in claim 1 wherein A is

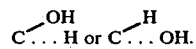

4. A compound as in claim 1 which is 21-desoxy-prednisolone-17α-alkyl-carbonate-21-chloride having 1 to 4 carbon atoms in the alkyl group.

5. A compound as in claim 1 which is 21-desoxy-prednisolone-17α-ethyl-carbonate-21-chloride.

6. A compound as in claim 1 which is 21-desoxy-prednisolone-17α-propyl-carbonate-21-chloride.

7. A compound as in claim 1 which is 21-desoxy-dexamethasone-17α-alkyl-carbonate-21-chloride having 1 to 4 carbon atoms in the alkyl group.

8. A compound as in claim 1 which is 21-desoxy-dexamethasone-17α-ethyl-carbonate-21-chloride.

9. A compound as in claim 1 which is 21-desoxy-dexamethasone-17α-propyl-carbonate-21-chloride.

10. A compound as in claim 1 which is 21-desoxy-prednisolone-17α-n-butyl-carbonate-21-chloride.

11. A compound as in claim 1 which is 21-desoxy-dexamethasone-17α-n-butyl-carbonate-21-chloride.

12. A pharmaceutical composition for the treatment of inflammatory dermatosis which comprises an effective amount of a compound as in claim 1 and a pharmaceutically-acceptable carrier therefor.

13. The method of treating inflammatory dermatosis in a human or animal suffering therefrom which method comprises locally or topically administering an effective amount of a compound as in claim 1.

* * * * *